| United States Patent [19] | [11] 4,011,251 |
|---|---|
| Tjurin et al. | [45] Mar. 8, 1977 |

[54] METHOD OF PREPARING ESTERS OF GLYCEROL AND POLYGLYCEROLS AND C5–C9 MONOCARBOXYLIC FATTY ACIDS

[76] Inventors: Boris Konstantinovich Tjurin, prospekt Oktyabrya, 71, kv. 116; Appolon Lukich Momot, prospekt Lenina, 26, kv. 2; Nikolai Lvovich Volodin, ulitsa Revoljutsionnaya, 7, kv. 12; Valentina Trofimovna Peremitina, prospekt Oktyabrya, 27, kv. 53; Anna Vasilievna Evdokimova, ulitsa Druzhby, 68, kv. 109; Vyacheslav Petrovich Churov, ulitsa Zheleznodorozhnaya, 14, kv. 9, all of Sterlitamak, Bashkirskaya ASSR; Samuil Markovich Krugly, ulitsa Khlobystova, 6, kv. 14, Moscow; Gabdulbar Garifzyanovich Garifzyanov, ulitsa Revoljutsionnaya, 7, kv. 25, Sterlitamak, Bashkirskaya ASSR, all of U.S.S.R.

[22] Filed: Mar. 13, 1975

[21] Appl. No.: 557,948

[52] U.S. Cl. .......................... 260/410.6; 260/488 J
[51] Int. Cl.$^2$ ...................... C09F 5/08; C11C 3/00
[58] Field of Search ........... 260/410.8, 488 J, 410.6

[56] References Cited

UNITED STATES PATENTS

| 2,309,949 | 2/1943 | Gooding | 260/410.8 |
|---|---|---|---|
| 2,677,700 | 5/1954 | Jackson | 260/488 J |
| 2,879,281 | 3/1959 | Brokaw | 260/410.8 |
| 2,958,706 | 11/1960 | Hurwitz | 260/488 J |
| 3,637,774 | 1/1972 | Babayan | 260/488 J |

OTHER PUBLICATIONS

Kirk–Othmer Encyclopedia of Chem. Tech. 2nd Ed., vol. 10, pp. 624–625.

*Primary Examiner*—Winston A. Douglas
*Assistant Examiner*—John F. Niebling
*Attorney, Agent, or Firm*—Steinberg & Blake

[57] ABSTRACT

The method of preparing esters of glycerol and polyglycerols with monocarboxylic fatty acids having from 5 to 9 carbon atoms consists in that glycerol and polyglycerols are reacted with monocarboxylic fatty acids, having from 5 to 9 carbon atoms at a temperature of 140°–210° C with continuous distillation of water that is present in the reaction zone. Glycerol and polyglycerols are introduced into the reaction as part of still bottoms of the process of distillation of synthetic glycerol obtained by the chlorine method, and containing sodium hydroxide and sodium chloride. The resultant reaction mixture contains the end product, which is isolated by any known method.

3 Claims, No Drawings

METHOD OF PREPARING ESTERS OF GLYCEROL AND POLYGLYCEROLS AND C5–C9 MONOCARBOXYLIC FATTY ACIDS

This invention relates to methods of preparing esters of polyatomic alcohols, and more particularly glycerol and polyglycerols, and monocarboxylic fatty acids having from 5 to 9 carbon atoms.

Said esters are widely used as plasticizing agents in the manufacture of polymers, for example, polyvinyl chloride, nitrocellulose, and as lubricating oils.

Methods are known in the prior art for preparing esters of polyatomic alcohols and monocarboxylic fatty acids. But they employ expensive raw materials, such as pentaerythritol, iso-alcohols, phthalic anhydride.

The above esters possess some valuable properties. They give high frost-resistance, tensile strength to polymers, and favourably affect the congellation point and flash point of lubricating oils.

Most popular methods of preparing said ester are those based on the reaction of esterification of polyatomic alcohols with monocarboxylic fatty acids. The reaction is effected at elevated temperatures in the presence of a catalyst with simultaneous removal of water, that is present in the reaction zone.

Known in the art is a method for preparing esters of polyatomic alcohols and monocarboxylic fatty acids, having from 5 to 9 carbon atoms, (for example from 7 to 9 carbon atoms). Pentaerythritol is used as a polyatomic alcohol. The method consists in the interaction of pentaerythritol with said acids at a temperature of 140° – 210° C.

The process is continued for 8–60 hours in a current of a noble gas with continuous removal of water that is present in the reaction zone. To accelerate the esterification reaction, and to increase the yield of the end product, the process is carried out in the presence of zinc oxide taken in the quantity of 0.2 per cent of the weight of acid.

The resultant reaction mixture is processed with sulphuric acid to decompose zinc soaps that are formed in the reaction, and then washed with water and dried in vacuum. Unreacted acids are then removed by vacuum distillation. The remaining unreacted acids are neutralized with an aqueous solution of alkali. The obtained mixture is processed with water, dried in vacuum, and filtered to remove mechanical admixtures.

The disadvantage of the method is the necessity to remove zinc oxide after the esterification process by processing the reaction mixture with sulphuric acid and water. The washings contain considerable quantities of zinc salts and the yield of the end product thus lowers to 60–70 per cent. Special means are required to decontaminate effluents containing zinc salts. Moreover, soft compounds made out of polymers containing a mixture of ester obtained by this method have insufficiently high physico-chemical properties.

The object of this invention is to provide a method of preparing esters of glycerol and polyglycerols and $C_5$–$C_9$ monocarboxylic fatty acids that would make in possible to widen the list of raw materials, and would increase the yields of product having better quality.

In accordance with these and other objects the invention consists in that said glycerol and polyglycerols are reacted with $C_5$–$C_9$ monocarboxylic fatty acids at a temperature of 140°–210° C with continuous distillation of water, that is present in the reaction zone, with formation of a reaction mixture containing the end product, and isolation of the end product. According to the invention, said glycerol and polyglycerols are part of still residue of the process of distillation of synthetic glycerol produced by the chlorine method, containing also sodium hydroxide and sodium chloride.

Making use of still residues obviates the need of using catalysts in the process of containing esters of polyatomic alcohols and $C_5$–$C_9$ monocarboxylic fatty acids, since the still residues contain sodium hydroxide and sodium chloride that produce catalytic action.

Sodium hydroxide and sodium chloride should not however be contained in excess, since this involves enlargement of the volume of apparatus and increases energy consumption, (sodium chloride) and excess consumption of monocarboxylic fatty acids (sodium hydroxide). In order to decrease their content, it is recommended that still residues, before their interaction with $C_5$–$C_9$ monocarboxylic fatty acids, should be processed with water taken at a ratio of 3–5 : 1 (still residue : water). Glycerol and polyglycerols, sodium hydroxide and partly sodium chloride are dissolved in this process. The resultant mixture is then processed with hydrochloric acid or hydrogen chloride to pH of the medium of 7.1 – 10, sodium hydroxide is partly neutralized to form additional quantities of sodium chloride, which is removed, for example, by filtration.

In order to increase the yield of the end product, and to improve its physico-chemical properties, it is recommended that the process of interaction of glycerol and polyglycerols with $C_5$ – $C_9$ monocarboxylic fatty acids should be carried out in the presence of activated carbon, which is taken in the quantity of 0.1 – 2 percent of the weight of the starting reactants (namely, monocarboxylic fatty acids, glycerol and polyglycerols).

The advantage of the proposed method is that new raw material, which is actually wastes of the process of manufacture of synthetic glycerol by the chlorine method, is used. Making use of such raw material — still residue of the process of distillation of synthetic glycerol — widens the list of raw materials in the manufacture of esters of polyatomic alcohols and monocarboxylic fatty acids having from 5 to 9 carbon atoms, and removes the necessity of using expensive raw materials. As has been said, still residues, alongside with glycerol and polyglycerols, contain also sodium hydroxide and sodium chloride. Utilization of such still residues removes the danger of contamination of effluents. The presence of these admixtures does not affect the properties of the end product and accelerates the esterification process.

The yield of the end product, obtained by the proposed method, is sufficiently high — 87 to 94 percent. The obtained product is a highly effective plasticizer. It is well compatible, for example, with polyvinyl chloride, nitrocellulose. Films of cable compounds, containing esters obtained by the proposed method, possess better physico-chemical properties that cable compound films containing dialkyl phthalates, or esters of pentaerythritol and $C_7$–$C_9$ monocarboxylic fatty acids. Comparative data are given in the Table below.

Table

| Properties of soft cable compound | Plasticizing agent | | |
|---|---|---|---|
| | Esters of pentaery-thritol and C₇-C₉ monocarboxylic fatty acids | dialkyl phtha-late | ester according to inven-tion |
| Tensile strength, kg/sq . cm | 170 | 170 | 185 |
| Specific elongation, % | 258 | 280 | 290 |
| Frost resistance, ° C | −39 | −40 | −40 to −50 |
| Decomposition point, ° C | 250 | 200 | 250 |
| Loss on heating, % | 1.8 | 1.8 | 1.8 |
| Colour fastness at 0° C, hrs | 96 | 96 | 96 |
| Ageing resistance at 70° C, hrs | 400 | 400 | over 400 |

The conditions for preparing soft cable compounds are similar in all cases. The composition of the films is parts by weight:

| | |
|---|---|
| polyvinyl chloride resin (suspension) | 100 |
| plasticizer | 60 |
| tricresyl phosphate | 10 |
| lead silicate | 15 |
| calcium stearate | 3 |
| carbon black | 1 |

The tabulated data show that cable compounds manufactured with esters obtained by the proposed method, possess better plasticizing properties (tensile strength, specific elongation, decomposition point, ageing resistance) compared with the other cable compounds.

The process of preparing esters of polyatomic alcohols and monocarboxylic acids having from 5 to 9 carbon atoms is effected as follows.

A three-neck flask provided with a stirrer, Dean and Stark receiver, and a thermometer, is loaded with still residues of the distillation of synthetic glycerol, obtained by the chlorine method, monocarboxylic fatty acids having from 5 to 9 carbon atoms, and activated carbon (if necessary). The reaction is carried out at a temperature of 140°–210° C for 2–8 hours, in a current of a noble gas with continuous distillation of water which is present in the reaction zone. Nitrogen can be used, for example, as the noble gas. The resultant reaction mixture contains the end product which is isolated by the known technique. To this end, the reaction mixture is cooled and sodium chloride is separated from it, for example by filtration. If the process is carried out in the presence of activated carbon, the latter is separated by filtration together with sodium chloride. Sodium chloride is washed with water, as a result of which two layers are produced: — the lower aqueous layer and the upper organic layer. The layers are separated and the organic layer is added to the filtrate, after which the mixture is distilled in vacuum to remove unreacted monocarboxylic fatty acids. Aqueous alkali solution, for example, a 3–5 percent sodium hydroxide solution, is added to the remaining filtrate to neutralize monocarboxylic acids that may remain unreacted. The obtained mixture is washed with water to neutral reaction, dried in vacuum, and mechanical admixtures are separated by filtration.

In order to decrease the sodium hydroxide and sodium chloride contents of the still residues utilized in the process they are first washed with water, then with hydrochloric acid or hydrogen chloride to pH of the medium of 7.1–10, with subsequent removal of sodium chloride (which is in the solid state) for example by filtration.

For a better understanding of the invention the following examples of its practical embodiment are given by way of illustration.

EXAMPLE 1

A flask is loaded with 150 g of still residues of the process of distillation of synthetic glycerol obtained by the chlorine method, containing 9.4 percent by weight of glycerol, 26.8 percent by weight of polyglycerols, 6.8 percent by weight of sodium hydroxide, 57 percent by weight of sodium chloride, and 195 g of synthetic monocarboxylic fatty acids having from 7 to 9 carbon atoms. The mixture is heated to a temperature of 140° – 210° C for 8 hours, with continuous removal of water, in a current of nitrogen. The resultant reaction mixture is cooled and sodium chloride is separated from it by filtration. Sodium chloride is washed with water to obtain a mixture consisting of two layers: — the lower aqueous layer and the upper organic layer. The filtrate is joined with the organic layer and distilled in vacuum to remove unreacted monocarboxylic fatty acids. To the remaining filtrate is added an aqueous solution of sodium hydroxide having the concentration of 3–5 percent to neutralize remaining unreacted monocarboxylic acids, after which it is washed with water to neutral reaction and dried in vacuum. The yield is 177 g (80 percent) of the end product.

The product has the following physico-chemical properties:

| | |
|---|---|
| acidity, mg KOH/g | 0.4 |
| ester value, mg KOH/g | 360 |
| refractive index | 1.4510 |
| density, g/cc | 0.971 |
| kinematic viscosity centistokes | 54 – 58 |
| flash point, ° C | 258 |

EXAMPLE 2

A flask is loaded with 150 g of still residues of the process of distillation of synthetic glycerol obtained by the chloride method, consisting of 8 percent by weight of glycerol, 28.2 percent by weight of polyglycerols, 6 percent by weight of sodium hydroxide, and 57.8 percent by weight of sodium chloride, and water in the ratio of 3:1 (still residue: water). The obtained mixture is processed with hydrochloric acid or hydrogen chloride, until the alkali content of the mixture is 2 percent by weight. Sodium chloride is then removed from the mixture by filtration.

The obtained mixture and 195 g of monocarboxylic fatty acids having from 7 to 9 carbon atoms are loaded into the reaction flask, and the end product is isolated as described in Example 1. The yield of the end product is 194.2 g (87.4 percent). The physico-chemical properties of the end product are similar to those specified for the product obtained in Example 1.

EXAMPLE 3

Still residues of the process of distillation of synthetic glycerol obtained by the chlorine method (150 g) contain the following components: 5 percent by weight of glycerol, 31.2 percent by weight of polyglycerols, 5 percent by weight of sodium hydroxide and 58.8 percent of sodium chloride. The still residue is processed with water, as in Example 2, and hydrochloric acid, until the alkali content of the mixture is 0.05 percent by weight, with subsequent separation of the obtained mixture by filtration.

The flask is loaded with the obtained mixture, 194 g of $C_7$–$C_9$ monocarboxylic fatty acids, and 2.5 g of activated carbon. The end product is prepared by the procedure described in Example 1 within 4–8 hours.

The end product is isolated from the obtained reaction mixture as described in Example 1, except that activated carbon is also removed from the mixture together with sodium chloride.

The yield of the end product is 210 g (94 percent). The physico-chemical properties of the end product are similar to those of the product obtained in Example 1.

EXAMPLE 4

100 g of still residues of the process of distillation of synthetic glycerol obtained by the chlorine method, contain the following components: 9.4 percent by weight of glycerol, 26.8 percent by weight of polyglycerols, 6.8 percent by weight of sodium hydroxide, and 57 percent by weight of sodium chloride. The still residue is processed with water taken in the ratio of 5:1 (still residue : water). The obtained mixture is processed with hydrochloric acid or hydrogen chloride until the alkali content is 0.03 percent by weight, with subsequent separation of sodium chloride from the obtained mixture by filtration.

The reaction flask is loaded with the obtained mixture, 109 g of $C_5$–$C_6$ monocarboxylic fatty acids, and 0.76 g of activated carbon. The end product is obtained and isolated by the same procedure as described in Example 3.

The yield of the end product is 109.5 g (94 percent). The product has the following physico-chemical properties:

| | |
|---|---|
| acid number, mg KOH/g | 0.5 |
| ester number, mg KOH/g | 380 |
| density, g/cc | 0.965 |
| kinematic viscosity, cs | 49 |
| flash point, °C | 245 – 250 |

EXAMPLE 5

100 g of still residue of the process of distillation of synthetic glycerol obtained by the chlorine method, having the composition similar to that specified in Example 4, are processed with water taken in the ratio of 4:1 (still residue: water). The obtained mixture is processed with hydrochloric acid or hydrogen chloride, until the alkali content is 0.02 percent by weight, with subsequent separation of sodium chloride from the obtained mixture by filtration.

The reaction flask is loaded with the obtained mixture, 120.75 g of $C_5$–$C_9$ monocarboxylic fatty acids, and 1.6 g of activated carbon. The end product is obtained and isolated by the procedure described in Example 3.

The yield of the end product is 126 g (93 percent). The product is characterized by the following physico-chemical properties:

| | |
|---|---|
| acid number mg KOH/g | 0.4 – 0.5 |
| ester number, mg KOH/g | 370 |
| density, g/cc | 0.97 |
| kinematic viscosity, cs | 52 |
| flash point, °C | 250 |

With processing the still residue with water in the selected ratio, and then with hydrochloric acid or hydrogen chloride as specified in Examples 2, 3, 4 and 5, the pH of the medium is 7.1 – 10.

EXAMPLE 6

A flask is loaded with 150 g of still residue of the process of distillation of synthetic glycerol obtained by the chlorine method. The composition of the still residue is as follows: 3.5 percent by weight of glycerol, 31.7 percent by weight of polyglycerols, 6.8 percent by weight of sodium hydroxide, and 58 percent of sodium chloride. Added to the still residue are also 195 g of $C_7$–$C_9$ monocarboxylic fatty acids and 3.75 g of activated carbon. The end product is prepared and isolated by the procedure as described in Example 1, except that activated carbon is also separated from the reaction mixture together with sodium chloride.

The yield of the end product is 190 g (85 percent).

The physico-chemical properties of the end product are the same as those of the product obtained in Example 1.

We claim:

1. Method of producing esters of glycerol and polyglycerols with $C_5$–$C_9$ monocarboxylic fatty acids which comprises reacting the still residue resulting from the distillation of synthetic glycerol produced by a chlorine method and containing in said residue glycerol, polyglycerols, sodium hydroxide and sodium chloride with $C_5$–$C_9$ monocarboxylic fatty acids at a temperature of 140° – 210° C with continuous distillation of water present in the reaction zone, thus forming a reaction mixture containing the corresponding esters, and isolating said esters from the reaction mixture.

2. The method of claim 1, wherein said still residue before being reacted with $C_5$ – $C_9$ monocarboxylic fatty acids, is processed with water taken in the weight ratio of still residue to water of 3–5 : 1 and, then with a reagent selected from the group consisting of hydrochloric acid and hydrogen chloride to pH of the medium of 7.1 – 10, which subsequent removal of precipitated sodium chloride.

3. The method of claim 1, wherein the reaction of said glycerol and polyglycerols with $C_5$ – $C_9$ monocarboxylic fatty acids is carried out in the presence of activated carbon taken in the quantity of 0.1 – 2 percent of the weight of the mixture of the starting reactants.

* * * * *